(12) United States Patent
Hauser

(10) Patent No.: US 9,452,178 B1
(45) Date of Patent: Sep. 27, 2016

(54) ACNE FORMULATIONS, TREATMENTS, AND PRESSURE SENSITIVE PATCHES FOR DELIVERY OF ACNE FORMULATIONS

(71) Applicant: SatisPharma, LLC, Boulder, CO (US)

(72) Inventor: Ray L. Hauser, Boulder, CO (US)

(73) Assignee: Satispharma, LLC, Boulder, CO (US)

( * ) Notice: Subject to any disclaimer, the term of this patent is extended or adjusted under 35 U.S.C. 154(b) by 0 days.

(21) Appl. No.: 15/004,698

(22) Filed: Jan. 22, 2016

Related U.S. Application Data

(63) Continuation-in-part of application No. 14/521,284, filed on Oct. 22, 2014, now abandoned.

(51) Int. Cl.
| | |
|---|---|
| *A61F 13/02* | (2006.01) |
| *A61L 15/16* | (2006.01) |
| *A61K 31/60* | (2006.01) |
| *A61K 9/70* | (2006.01) |
| *A61K 47/26* | (2006.01) |
| *A61K 47/32* | (2006.01) |

(52) U.S. Cl.
CPC .............. *A61K 31/60* (2013.01); *A61K 9/703* (2013.01); *A61K 47/26* (2013.01); *A61K 47/32* (2013.01)

(58) Field of Classification Search
None
See application file for complete search history.

(56) References Cited

U.S. PATENT DOCUMENTS

| | | | |
|---|---|---|---|
| 3,026,248 A | 3/1962 | Noseworthy et al. | |
| 4,316,902 A * | 2/1982 | Yu | A61K 8/31 424/60 |
| 4,784,999 A | 11/1988 | Angersbach et al. | |
| 4,877,773 A | 10/1989 | Turner | |
| 4,895,727 A | 1/1990 | Allen | |
| 4,978,531 A * | 12/1990 | Yamazaki | A61K 9/7053 424/448 |
| 5,919,487 A * | 7/1999 | Simonnet | A61K 8/11 424/47 |
| 5,976,565 A * | 11/1999 | Fotinos | A61K 8/0208 424/404 |
| 6,197,823 B1 | 3/2001 | Barr et al. | |
| 6,348,501 B1 | 2/2002 | Holt et al. | |
| 6,419,913 B1 | 7/2002 | Niemiec et al. | |
| 6,482,839 B1 | 11/2002 | Thornfeldt | |
| 6,573,302 B1 | 6/2003 | Holt et al. | |
| 6,653,352 B2 | 11/2003 | Barr et al. | |
| 6,693,100 B1 | 2/2004 | Zarmanian et al. | |
| 6,812,254 B1 | 11/2004 | Barr et al. | |
| 7,271,182 B2 | 9/2007 | Kamiyama et al. | |
| 7,709,497 B2 | 5/2010 | Christensen, IV et al. | |
| 7,879,344 B2 | 2/2011 | Feldkamp et al. | |
| 2006/0216318 A1 | 9/2006 | Majmudar | |
| 2006/0235080 A1 | 10/2006 | Weissbach et al. | |
| 2007/0258935 A1 | 11/2007 | McEntire et al. | |
| 2007/0269393 A1 | 11/2007 | Wepfer | |
| 2007/0286815 A1 * | 12/2007 | Bechtold | A61K 9/008 424/45 |
| 2008/0058369 A1 | 3/2008 | Allen et al. | |
| 2008/0255186 A1 | 10/2008 | Christensen et al. | |
| 2008/0275078 A1 | 11/2008 | Cook et al. | |
| 2009/0053290 A1 | 2/2009 | Sand et al. | |
| 2009/0123504 A1 | 5/2009 | Feldkamp et al. | |
| 2009/0318494 A1 | 12/2009 | Allen et al. | |
| 2009/0325952 A1 | 12/2009 | Allen et al. | |
| 2011/0184016 A1 | 7/2011 | Lerner et al. | |
| 2013/0085166 A1 | 4/2013 | Makra | |

FOREIGN PATENT DOCUMENTS

| | | |
|---|---|---|
| WO | 2011/075688 A1 | 6/2011 |
| WO | 2011/086458 A1 | 7/2011 |

OTHER PUBLICATIONS

Diez et al., Influence of d-limonene on the transdermal penetration of felodipine, European Journal of Drug Metabolism and Pharmacokinetics 1998.*
Burke, John, "Solubility Parameters: Theory and Application", The Book and Paper Group Annual, vol. 3, 1984, 41 pp.

* cited by examiner

*Primary Examiner* — Robert A Wax
*Assistant Examiner* — Quanglong Truong
(74) *Attorney, Agent, or Firm* — Sheridan Law, LLC; James A. Sheridan

(57) ABSTRACT

There are disclosed formulations, medicated skin treatments, methods of treating acne, pressure-sensitive patches with acne formulations, and skin treatments. In an embodiment, there is provided a formulation of a skin treatment effective in removal of sebum-formed oils from skin of a human body. The formulation includes glycerin, polyvinylpyrrolidone, salicylic acid, and two or more lipophilic vitamin anti-oxidants, and the polyvinylpyrrolidone in a crosslinked configuration by at least one of a chemical process or a radiation process. In an embodiment, there is provided pressure-sensitive adhesive patch configured for application over acne breakouts. The patch includes a fabric material or flexible plastic backing material. The patch includes a formulation carried by the fabric material or the flexible plastic backing material. The formulation is configured to provide a skin treatment effective in removal of sebum-formed oils from the skin of a human body. Other embodiments are also disclosed.

8 Claims, No Drawings

ACNE FORMULATIONS, TREATMENTS, AND PRESSURE SENSITIVE PATCHES FOR DELIVERY OF ACNE FORMULATIONS

REFERENCE TO PENDING PRIOR PATENT APPLICATION

This patent application is a continuation-in-part of pending prior U.S. patent application Ser. No. 14/521,284, filed Oct. 22, 2014 by Ray L. Hauser for ACNE FORMULATIONS, TREATMENTS, AND PRESSURE SENSITIVE PATCHES FOR DELIVERY OF ACNE FORMULATIONS.

The above-identified patent application is hereby incorporated herein by reference.

BACKGROUND

Three physiological effects contribute to the generation of acne pimples. The first is an excess production of sebum by the sebaceous glands and transported to the epidermis by the ducts of hair follicles. The second cause is the plugging of hair follicles by dead skin particles and/or external solid particles. The third cause is bacterial infection of accumulating sebum in these pilosebaceous follicles by anaerobic microorganisms including *Propionibacterium*. When these occur, the sebum accumulates, causes swelling, itching, growth of pustules or papules, redness of the skin, itching, and emotional distress. The acne pimple may finally burst, exuding a liquid or semi-solid. And it may heal with a permanent scar. Although doctors recommend against popping pimples and blackheads, many folks do so, often prematurely causing further damage.

The Food and Drug Administration lists accepted specific ingredients for treatment of acne, directed toward the second and third causes. Two treatments are directed toward bacterial infections are benzoyl peroxide (CAS #94-36-0) and sulfur (CAS #7704-34-9) or sulfur plus resorcinol (CAS #108-46-3). A treatment is also directed toward use of salicylic acid (CAS #69-72-7) as an exfoliant to prevent accumulation of dead skin particles that may clog the pores and cause accumulation of sebum where it can be attacked by the bacteria. The FDA has not approved any ingredient or system for minimizing or removing excess skin oils, but a number of astringent preparations have been marketed. These include clays, talcs, silicas, starches, polymers and similar materials. Alcohols and acetone are known to remove skin oils, but they often leave a dry skin that responds by promptly increasing production of sebum. Cosmetics applied to mask unsightly zits are generally cosmedogenic and may further aggravate the entrapment of sebum.

A number of products have been marketed for systemic treatment of acne by ingestion of pills containing antibiotics.

U.S. Pat. No. 6,120,756 discloses: "The primary etiologic factor in acne is now thought to be excessive sebum production. A treatment best able to modify this will be most efficacious. The present state of the art is such that treatment with systemic drugs in the only current way to control excessive sebum production."

Acne is a prevalent and distressing problem leading to a reported $2 billion annual market for treatment in the U.S. Most treatments are based on the FDA-approved active ingredients discussed above. Some include unapproved ingredients such as clays, corn starch, microbeads, titania and walnut shells, presumably to provide a scrubbing action, but with the risk of clogging pores and making the problem worse.

U.S. Pat. No. 6,093,408 discloses the use of silicone oil copolymer and silicone gum in an aqueous emulsion to help regulate production of sebum. Anti-infective ingredients are added, such as benzoyl peroxide and salicylic acid. To be an effective treatment, such an emulsion is applied to the skin and left in place, as implied by subject patent. Such a product is not found to be on the market at the present time.

An extensive investigation and analysis of human sebum has been accomplished by personnel of Johnson & Johnson, developers and marketers of many skin care products. (ref. Pappas, et al, "Sebum Analysis of Individuals With and Without Acne," *Dermatoendrocrinol* 2009 May-June 1(3): 157-161). Sebum consists of fatty acids, oily triglycerides and waxes. This reference reports that acne patients (both teenage and adult) had 59% more sebum than non-acne patients. The fatty acids have at least one unsaturated group (double bond in the hydrocarbon molecule) and the triglycerides from these oils are presumed to be similarly unsaturated. Of particular interest is the oil component of sebum, squalene, which is present at 12-15% in normal sebum but at 2.2 times as much in acne patients and this increase continues to be present in adult acne sufferers. This squalene is an unsaturated hydrocarbon with chemical formula $C_{30}H_{50}$ and it has six carbon double-bonds.

Johnson & Johnson and others purveying acne treatments have not used this information to develop and market a product comparable to the various embodiments disclosed herein despite their considerable research budgets.

The presence of double bonds in the molecules of mobile sapienic acid and sebaleic acid and in the higher molecular weight squalene plus the presence of a strong oxidizer and cross-linker (benzoyl peroxide) was troubling to this inventor who was well acquainted with the vulcanization of synthetic elastomers (EPDM and silicones particularly) by benzoyl peroxide at high temperature and was well acquainted with the slow decomposition of benzoyl peroxide in solutions at room temperature. The free radicals from benzoyl peroxide are standards in polymerization and cross-linking reactions at any temperature. If two mobile molecules of sebum and one free radical are in close proximity, the result may be a cross-linking reaction forming a new molecule with double the molecular weight and probably a new solid that the sebum ducts are not prepared to export normally. The body is good at moving liquids, but not solids in other than through the digestive system.

The oily triglycerides in sebum are only slightly different from linseed oil, used in paints for centuries because it oxidizes to a solid by cross-linking at its double bonds. Similar reactions are hypothesized to occur when the linoleic acid, sapienic acid, sebaleic acid and squalene of sebum react with benzoyl peroxide in a treatment intended to help minimize breakouts of acne. An acne treatment that combines benzoyl peroxide with clay may be making a product similar to linseed oil-based glazier's putty within the glands and ducts of the skin.

Squalene is a precursor to formation of low density cholesterol, another solid that can cause similar and more serious clogging of blood vessels.

The world needs a better treatment system for reducing the itches, inflammations, discolorations, scars and confidence problems caused by acne.

SUMMARY

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

In one embodiment, there is provided a formulation of a skin treatment effective in removal of sebum-formed oils from the skin of a human body, the formulation comprising glycerin, polyvinylpyrrolidone, salicylic acid, and two or more lipophilic vitamin anti-oxidants, and the polyvinylpyrrolidone in a crosslinked configuration by at least one of a chemical process or a radiation process.

In another embodiment, there is provided a pressure-sensitive adhesive patch configured for application over acne breakouts, the patch comprising a fabric material or flexible plastic backing material; a formulation carried by the fabric material or the flexible plastic backing material, the formulation configured to provide a skin treatment effective in removal of sebum-formed oils from the skin of a human body, the formulation including glycerin, polyvinylpyrrolidone, salicylic acid, and two or more lipophilic vitamin anti-oxidants, and the polyvinylpyrrolidone in a crosslinked configuration by at least one of a chemical process or a radiation process after application of the formulation onto the fabric material or the flexible plastic backing material.

In yet another embodiment, there is provided method of treating skin blemishes including acne by placing an oil-absorbing patch over an incipient or mature pimple for at least 6 hours, the method comprising providing a pressure-sensitive adhesive patch configured for application over acne breakouts, the patch comprising a fabric material or flexible plastic backing material; a formulation carried by the fabric material or the flexible plastic backing material, the formulation configured to provide a skin treatment effective in removal of sebum-formed oils from the skin of a human body, the formulation including glycerin, polyvinylpyrrolidone, salicylic acid, and two or more lipophilic vitamin anti-oxidants, and the polyvinylpyrrolidone in a crosslinked configuration by at least one of a chemical process or a radiation process after application of the formulation onto the fabric material or the flexible plastic backing material; placing the pressure-sensitive adhesive patch over an incipient or mature pimple for at least 6 hours; and removing the pressure-sensitive adhesive patch from the incipient or mature pimple after placement thereon for at least 6 hours.

In one embodiment, there is provided a formulation of a skin treatment effective in removal of sebum-formed oils from skin of a human body, the formulation comprising a solution or emulsion containing a medically acceptable solvent with a solubility parameter between 12 and 20 $MPa^{0.5}$, the solvent having a normal boiling temperature above 100° C., the solvent at a concentration exceeding 5%, and the solvent configured to treat skin of a human body.

In another embodiment, there is provided method of treating acne, the method comprising treating the skin with a solution or emulsion containing a medically acceptable solvent with a solubility parameter between 12 and 20 $MPa^{0.5}$ and having a normal boiling temperature above 100° C. and at a concentration exceeding 5%; allowing said formulation to remain on the skin for a time period of 0.5 to 3 minutes so as to create in the solution or emulsion an amount of residual formulation and absorbed skin oils; and blotting and wiping the skin surface to remove at least a portion of the residual formulation and the absorbed skin oils.

In another embodiment, there is provided an itch relieving composition as described in this inventor's U.S. Pat. No. 9,011,934 in a carrier medium having a solubility parameter between 30 and 45 $MPa^{0.5}$ and a boiling temperature exceeding 100° C. and containing multivalent cations in concentration exceeding 40 mmol/liter. Such itch-relieving composition may be combined with other embodiments herein.

In yet another embodiment, there is provided a method of treating acne, the method comprising applying a solution or emulsion containing a medically acceptable solvent with a solubility parameter between 12 and 20 $MPa^{0.5}$, the solvent having a normal boiling temperature above 100° C., the solvent at a concentration exceeding 5%, and the solution or emulsion configured to treat skin of a human body; and applying a formulation having an exfoliant of salicylic acid or glycolic acid at a concentration at least 0.5%.

In still another embodiment, there is provided a pressure-sensitive adhesive patch configured for treatment over individual acne breakouts, the patch including a formulation for treatment of acne, and the patch including a fabric or flexible plastic backing configured to direct the formulation to skin of a human body.

Various embodiments illustrate formulations that can be used separately or, in sequence, to provide cosmetic and pharmacologic benefits to human skin, particularly for minimization of distress from acne. An oil removal formulation is applied to the skin, allowed to penetrate the epidermis, and then is wiped off after dissolving both oil and wax components of sebum, concurrently leaving in the skin a medically acceptable replacement oil. The second treatment uses an FDA approved active ingredient, salicylic acid plus itch-relieving ingredients to provide comfort and exfoliation of dead skin. Preferably, the second treatment follows the oil removal treatment. The third treatment is a medicated adhesive patch applied over an active pimple to provide healing and masking an ugly zit.

Other embodiments are also disclosed.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Additional objects, advantages and novel features of the technology will be set forth in part in the description which follows, and in part will become more apparent to those skilled in the art upon examination of the following, or may be learned from practice of the technology.

DETAILED DESCRIPTION

Embodiments are described more fully below in sufficient detail to enable those skilled in the art to practice the system and method. However, embodiments may be implemented in many different forms and should not be construed as being limited to the embodiments set forth herein. The following detailed description is, therefore, not to be taken in a limiting sense.

Various embodiments relate to cosmetic and pharmaceutical compositions and methods for treatment of acne on human skin. These embodiments provide novel and original modes of addressing this basic problem of excessive sebum production by partial removal and replacement of the reactive oils.

Various embodiments are based first upon removal of excessive sebum from the skin and displacing it with a small amount of non-reactive oil that leaves the skin soft and supple rather than drying the skin as happens when washed with solvents such as acetone and alcohols.

Sebum oils have a low solubility parameter, a quantitative measure that can predict the behavior of different solvents and polymers. The solubility parameters of three major components of sebum have been calculated to be the following:

Sapienic acid 16.7 MPa$^{0.5}$
Sebaleic acid 16.3 MPa$^{0.5}$
Squalene 16.5 MPa$^{0.5}$ which is close to paraffin wax and polyethylene at 15.2 MPa$^{0.5}$ Liquids with similar solubility parameters can dissolve these chemicals easily. Toluene, octane and even acetone can dissolve these oils. However, these solvents are also quite flammable and volatile, representing an immediate fire hazard and they leave the skin quite dry and calling on the sebaceous glands to produce more skin lubricant.

There are few solvents that are medically acceptable and with similarly low solubility parameters and with low volatility such that they might remain as skin lubricants. These include silicone oils (e.g. dimethyl siloxane ca 15.2 MPa$^{0.5}$), fluoroethers (perfluoromethylethyl ether is 12.9 MPa$^{0.5}$) and d-limonene (16.5 MPa$^{0.5}$). The first of these two groups are relatively expensive. D-limonene is obtained by pressing or by steam distillation of orange peels and this byproduct from production from orange juice is available at a moderate cost. Its solubility parameter is found to be identical to that of squalene, the skin oil that continues to plague acne sufferers from teen years into adulthood. D-limonene has normal boiling temperature of 176° C. and its flash point exceeds 43° C., indicative of permanence and moderate safety. This is a unique combination of attributes ideally suitable for the present application. D-limonene has CAS #138-86-3 and UNII GFD7C86Q1W Two additional prospective solvents for sebum oils are butyl acetate and isoamyl acetate (banana oil), both of which are moderately priced. Their physical properties are:

n-Butyl Acetate CAS#123-86-4, UNII 464P5N1905, BP 126° C., solubility parameter 16.9 MPa$^{0.5}$
Isoamyl acetate CAS#123-92-2, UNII Z135787824, BP 142° C., solubility parameter 17.3

Either or both of these could be used by itself, in combination, or mixed with d-limonene, but butyl acetate represents a greater use hazard because of its lower flash point.

Another natural solvent, terpineol, is a prospect for dissolution of sebum oils. This is CAS#98-55-5 and UNII#GFD7C86Q1W. It has a solubility parameter of 16.7 MPa$^{0.5}$ and has a melting temperature of 35° C., just below body temperature. It has a boiling temperature of 217° and is not subject to oxidation as is limonene. Terpineol is reported by Oyedemi et al to be bactericidal to gram-positive bacterial at concentration above 0.5 volume percent. Tea tree oil is a similar natural product whose major component is terpinen-4-ol which has a solubility parameter calculated to be 16.7 MPa$^{0.5}$. Tea tree oil has bactericidal properties recognized by the National Institutes of Health and is reported to be as effective as benzoyl peroxide in some acne treatments.

Many vegetable oils (triglycerides) also have relatively low solubility parameters and olive oil or canola oil can probably dissolve sebum, but their residues will be chemically similar to the sebum itself and will be susceptible to the same problems caused by excess sebum. Even a fully hydrogenated cottonseed oil (94% saturated) could probably de-esterify by the effects of bacteria that attack sebum. The bacterial culprit is reported in U.S. Pat. No. 6,093,408 to be *Propionibacterium* (*Corynebacterium*). This anaerobic type of gram-positive bacteria (conventionally *P. acnes*) generates inflammatory fatty acids from the glycerides which then irritate the follicular wall, leading to rupture and inducing an inflamed lesion.

The sebum oil-dissolving solvent can be applied to the skin in a relatively pure form or it can be emulsified with water to form a smooth cream with other medicaments to provide a measure of anti-bacterial protection, anti-oxidant and itch relief, as described in examples below. The bacteria and oxidation protectants should be soluble in the sebum oil-dissolving solvent to be most effective, but there are few acceptable (approved by the FDA for acne treatment) antiseptic chemicals that are soluble in such solvents.

But after the excessive sebum is dissolved by the d-limonene or other appropriate solvent system, it should be removed. Thus application of the cream is followed about 1-2 minutes later by wiping the residuals from the skin with a tissue. Any residual d-limonene has a pleasant lemony aroma. Any residual isoamyl acetate has the pleasant aroma of banana oil.

Various embodiments use a second treatment to the skin to provide exfoliation in accord with FDA regulations in 21CFR333.310. This is based on a skin cream containing 0.5-2% salicylic acid. In the present instance, the salicylic acid is combined with a humectant and multivalent cations in accord with U.S. Pat. No. 9,011,934, "Multi-Purpose Anti-Itch Treatment," to minimize itching and attendant scratching. A moderate bactericide is preferably included to help prevent infection of any built-up of sebum, and an anti-oxidant is preferably included. L-ascorbic acid or preferably an ester thereof (such as ascorbyl palmitate or stearate) is the preferred anti-oxidant in one embodiment. Surfactant, colorant or fragrance may be added as desired.

In another embodiment, the active ingredient, salicylic acid, is combined with a pressure-sensitive adhesive applied to a skin-colored fabric. Such an adhesive is described in patent application Ser. No. 12/548,301, now abandoned, using a combination of glycerin and polyvinylpyrrolidone. Again, glycerin-soluble multi-valent cations may be combined with this mixture, along with bactericide and antioxidant. This patch is then applied over individual acne eruptions providing a mask with a blending skin color as well as continued medication to the eruption while in place. The adhesive of this patch is water-soluble.

Another embodiment is perceived as a sebum oil remover using almost 100% limonene or comparable solvent with a gellant to increase its viscosity. Silica aerogel may be an appropriate gellant if it can be effectively removed from the skin during the removal process to prevent the silica particles from plugging pores.

Another embodiment is a combination of ingredients for oil removal and for exfoliation in one application/removal process. This has the disadvantage of a shorter residence time on the skin for the salicylic acid Active Ingredient, but it has the advantage of prompt removal of dead skin cells along with the excess sebum oils.

One embodiment of this invention uses a water-soluble pressure-sensitive adhesive on a backing to form a patch. Such an adhesive is described in patent application Ser. No. 12/548,301, now abandoned, using a combination of glycerin and polyvinylpyrrolidone. Glycerin-soluble multi-valent cations may be combined with this mixture, along with bactericide, exfoliant, and antioxidant. This patch is applied over individual acne eruptions providing a mask with a blending skin color as well as continued medication to the eruption while in place. The adhesive of this patch is initially water-soluble, but is preferably cross-linked.

This pressure-sensitive adhesive formulation takes advantage of the reported complexing reaction between salicylic acid (an exfoliant accepted by FDA for treatment of acne in concentration 0.5 to 2.0 weight percent (21 CFR333.310). An opinion from one FDA specialist has informed the inventor that using salicylic acid in an adhesive patch represents a transdermal patch which would require formal clinical trials in order to prove its safety and efficacy prior to making any claims as a treatment for acne. The referenced publication by Lionda Rhein et al, of GlaxoSmithKlein, states that salicylic acid forms a complex with polyvinylpyrrolidone that prevents its permeation through the epidermis. The salicylic acid remains on the external surface of the skin where it functions as an exfoliant (as recognized by the FDA) and it not a transdermal medication. Costs and time for formal clinical trials are a major deterrent prior to marketing this type of product, a major advantage of this embodiment.

This information from GSK, purveyors of Duac gel, POanoxyl and Fabior acne medications, was undoubtedly read in 2004 and following years by other major pharmaceutical scientists. But we find no product on the market and no intellectual property using this technology complexing salicylic acid with high molecular weight PVP to make a safe and efficacious adhesive patch.

Another embodiment of this invention uses a pressure-sensitive adhesive on a backing to form a patch that effectively acts as a sponge for absorption of excess skin oils and concurrently supplies chemical treatment to a pimple to attack bacteria and to provide exfoliation of dead skin. This pressure-sensitive adhesive may preferably be a mixture of polybutenes and polyisobutylenes with tackifier and plasticizer, or may be a commercial silicone pressure-sensitive adhesive such as Dow-Corning 282. Polybutenes have solubility parameter about 15.8 $MPa^{0.5}$ and silicones have a solubility parameter about 15.3 $MPa^{0.5}$. Both are good absorbers of skin oils. Dow Corning 282 solution adhesive is described as containing CAS 68988-56-7 trimethylated silica, CAS1330-20-7 xylene, CAS70131-67-8 hydroxy terminated dimethyl siloxane, CAS 100-41-4 ethylbenzene, CAS556-67-2octametylcyclopentasiloxane, CAS3555-47-3 tetra(trimethylsiloxy)silane, and 18-88-3 toluene. Of course the xylene and toluene solvents evaporate after the solution is applied to a backer or to a release film.

The following definitions are used herein:

Acne, a pilosebaceous disease characterized by comedo, papules, inflamed nodules and/or superficial pus filled cysts.

Anti-microbial, bactericide, or antiseptic, a compound capable of destroying or inhibiting the growth of microorganisms 'Caine family, a popular term for a group of essentially interchangeable local anesthetics, which includes benzocaine, carbocaine, lidocaine, xylocaine, and others Emulsion, a system of one liquid dispersed as droplets in a second immiscible liquid FDA approved Active Ingredient, a component in a medication for a specific use as identified by the U.S. Food and Drug Administration in 21 CFR Lipophilic, soluble in solvents having a solubility parameter less than 25 $MPa^{0.5}$.

Flash Point, the lowest temperature at which a material may burst into flame in a normal atmosphere Peel strength, the adhesive restraining force per unit width in a 180° peel of backing material freshly bonded to sheepskin rigidly adhered to a rigid aluminum panel with a peeling rate of 2.3 cm/sec.

Skin blemish, any abnormal discoloration, protrusion or mark that diminishes attractiveness Solubility Parameter, a measure of solution characteristics of solvents and polymers based on the cohesive energy density, the heat of vaporization at 25° C. per unit volume, usually reported as $(calories/cc)^{0.5}$ or $MPa^{0.5}$ Viscosity, a measure of the resistance to flow, here as measured by a Brookfield viscometer using a #3 spindle rotating at 6 rpm, usually reported in centipoise units.

EXAMPLES

Example 1

An emulsion was prepared for removal of skin oils by combining limonene solvent, isopropyl myristate skin penetration enhancer, lidocaine pain reliever and benzethonium chloride anti-microbial, and nonioinic surfactant in water with a polyacrylate thickener and diazolidinyl urea preservative.

| | | |
|---|---|---|
| d-Limonene | 20% | sebum solvent |
| Isopropyl myristate | 1% | skin penetration enhancer |
| Lidocaine | 0.15% | local pain reliever |
| Polysorbate 80 | 2% | surfactant/emulsifier |
| Benzethonium chloride | 0.1% | bactericide |
| Water | 75.9% | diluent |
| Polyacrylate Ultrez 21 | 0.5% | viscosity modifier |
| Germall Plus, fungicide | 0.1% | (diazolidinyl urea + iodopropanyl butylcarbamate) fungicide |
| NaOH | 0.25% | alkalinity |

The first four ingredients were pre-mixed and were added to the water with rapid stirring, forming an emulsion quickly.

This gave a viscosity appropriate for packaging and dispensing with a conventional squeeze tube. It had a smooth feel and was easy to apply to the face, and left the skin feeling smooth after wiping with a tissue. A comparable emulsion was subjected to four freeze-thaw cycles at 0° C./22° C. without breaking the emulsion.

An emulsion of this nature and the following three examples is considered appropriate for wiping onto the skin, rubbing it in or letting it soak in for a brief period of time, and then wiping off the skin, to help dissolve and remove an excess of skin oils.

Example 2

A similar emulsified formulation was prepared for removing skin oils but with a lower viscosity for dispensing with a pump from a bottle and including sufficient benzoyl peroxide to qualify as an acne treatment under 21 CFR 333.310:

| | | |
|---|---|---|
| d-Limonene | 20% | |
| Diethylene glycol monomethyl ether | 1% | skin penetration enhancer (Transcutanol) |
| Lidocaine | 0.15% | |
| Polysorbate 80 | 2% | |
| Benzoyl peroxide | 2.5% | |
| Water | 76.3% | |
| Polyacrylate Ultrez 21 | 0.25% | |
| Germall Plus | 0.1% | |
| NaOH | 0.175% | |

The first five ingredients were prepared as a solution and were added to the water with rapid stirring, forming a stable emulsion. The product had a viscosity of 5500 centipoise, suitable for packaging in a bottle with a pump dispenser. It had a pH of 8.7 and had a good feel on the skin.

Example 3

An emulsion was prepared using the following formulation using a blend of sebum-dissolving solvents but without benzoyl peroxide:

| | | |
|---|---|---|
| d-Limonene | 25% | |
| Isoamyl acetate | 25% | cosolvent |
| Tea tree oil | 5% | co-solvent and bactericide |
| Transcutanol | 2% | |
| Lidocaine | 0.15% | |
| Polysorbate 80 | 2% | |
| Ascorbyl palmitate | 0.5% | |
| Water | 42.5% | |
| Polyacrylate Ultrez 21 | 0.5% | |
| Benzethonium chloride | 0.15% | |
| Germall plus | 0.1% | |
| Phenoxyethanol | 0.6% | |
| NaOH | 0.3% | |

This formulation does not meet present FDA requirements as an acne treatment and is best described as a bactericidal wash

Example 4

| | | |
|---|---|---|
| d-Limonene | 25% | |
| Isoamyl acetate | 25% | cosolvent |
| Tea tree oil | 5% | co-solvent and bactericide |
| Transcutanol | 2% | |
| Lidocaine | 0.15% | |
| Parachloro meta xylenol | 0.10% | (antiseptic) |
| Polysorbate 80 | 2% | |
| Ascorbyl palmitate | 0.5% | |
| Water | 43.3% | |
| Polyacrylate Ultrez 21 | 0.3% | |
| Benzethonium chloride | 0.05% | |
| Salicylic acid | 0.5% | |
| Germall plus | 0.1% | |
| Phenoxyethanol | 0.6% | |
| NaOH | 0.31% | |

This emulsion formulation includes salicylic acid and can be considered an appropriate acne treatment per 21CFR333.310(d). It had pH=6.4 (within normal range for skin) and viscosity of 6200 cp.

Example 5

A cream treatment was prepared for treating acne by remaining on the skin using the following formulation meeting FDA requirements for the active ingredient:

| | | |
|---|---|---|
| Glycerin | 15% | solvent, humectant |
| Transcutanol | 3% | |
| Xanthan, Kelco CG-SFT | 0.3% | viscosity modifier |
| Water | 75% | |
| Aspirin | 1% | |
| Zinc acetate hydrate | 1% | pain reliever, moisture absorber |
| Epsom salt | 1% | pain reliever, moisture absorber |
| Salicylic acid | 1% | active ingredient |
| Aloe gel 200x | 2% | skin improver |
| Benzethonium chloride | 0.1% | |
| Phenoxyethanol | 0.6% | preservative |
| Lidocaine | 0.15% | |
| Germall + preservative | 0.1% | |
| Sodium hydroxide | 1% | alkalinity |

This formulation had a pH of 4.1, within the range of normal skin, and about 700 centipoise viscosity

Example 6

A patch was prepared using a tan cotton/spandex poplin fabric (174 gm/sq·m.) coated on one side with the following formulation of a pressure-sensitive adhesive:

| | | |
|---|---|---|
| Glycerin | 57.2% | |
| Transcutanol | 10% | |
| Tea tree oil | 1% | |
| Polyvinylpyrrolidone 1.3 million Daltons | 20% | (adhesive polymer) |
| Jaguar gum VP120 | 8% | (gellant and adhesive) |
| Salicylic acid | 0.5% | |
| Zinc acetate hydrate | 0.5% | |
| Epsom salt | 0.5% | |
| Aloe gel 200x | 1% | skin improver |
| Ascorbyl palmitate | 0.5% | antioxidant |
| Lidocaine | 0.15% | |
| Phenoxyethanol | 0.6% | |
| Germall+ | 0.1% | |

Denatured alcohol was added, 75 grams/100 grams of the formulation to facilitate mixing. After evaporation of ⅓ of the alcohol, it had a viscosity suitable for draw-down application onto a release film, Rayven Rf-7000-41. The drawdown blade had a gap 0.015 inch and applied about 187 grams of dry adhesive per sq. meter of film. After the alcohol had evaporated, the fabric was placed on the adhesive and the uncoated side of the fabric was sprayed with a water repellant, 3M Scotchgard, and the fabric was then cut into circles 1" diameter with a steel punch. A similar patch was applied to cover an active acne spot to provide temporary cosmetic masking and medication to the skin injury. The patch remained in place for about 24 hours, and the zit was barely discernible a day later.

In production, an adhesive similar to this example could be melt-extruded directly to a release film or perhaps directly to the fabric, avoiding use of flammable solvent. Alternatively, water may be used as alternative to alcohol.

Prior formulations have shown that the high molecular weight of the PVP was imperative in forming a suitable pressure-sensitive adhesive. This formulation is thought to meet FDA requirements in 21CFR333.310 without further clinical testing by virtue of its unique combination of the very high molecular weight PVP with salicylic acid.

If mandelic acid were to be substituted for salicylic acid, the patch could be considered a cosmetic treatment for skin blemishes, rather than a medicated treatment for acne.

Example 7

| | | |
|---|---|---|
| Polyethylene glycol 400 | 34.5% | |
| Triethanolamine | 0.5% | |
| Polyvinylpyrrolidone 1.3 million Daltons | 57% | |
| Salicylic acid | 0.5% | |
| Aloe gel 200x | 4% | skin improver |
| Ascorbyl palmitate | 2% | antioxidant |
| Germall+ | 1% | |
| Denatured alcohol as needed for dissolution and application, approximately 3x PVP concentration | | |

This mix was applied by a drawdown onto the release film of Example 6 using a gap of 1.27 mm, allowed to dry and was covered with a tan colored fabric. The dried adhesive weight was about 48.8 mg/sq·cm. and its thickness was 0.13 mm. Its bond strength to sheepskin was 430 grams/cm width. The dosage of salicylic acid was about 0.24 mg/sq·cm.

Example 8

A pressure-sensitive adhesive formulation was prepared using the following ingredients to evaluate the merits of cross-linking the PVP polymer:

| | |
|---|---|
| Glycerin | 6 grams |
| Water | 45 grams |
| PVP 1.3 million Daltons | 14 grams |
| Sodium persulfate | 0.28 grams |
| Sodium hydroxide | 0.10 grams |

This mix had a pH about 10. It was applied to release film with a drawdown having a gap of 0.76 mm and was allowed to dry. Its dry adhesive weight was about 14 mg/sq·cm and its thickness about 0.08 mm. A portion was heated in an oven at 275° F. for 30 minutes. Peel strength from sheepskin was about 300 gm/cm width. Disks of this product were placed in water and the PVP was observed to swell, but it did not dissolve in the water, confirming the merits of a cross-linked pressure-sensitive adhesive, which should be less sensitive to variations in ambient humidity than uncross-linked PVP. In production, cross-linking may be better accomplished using radiation rather than chemical reactant.

Example 9

An oil-absorbing patch was prepared for application over a pimple in the evening and for removal in the morning (or for leaving in place if the pimple is ugly) with the following formulation:
Polyisobutylene BASF Oppanol 80 (800,000 Daltons), 10 grams
Toluene, 80 grams
Polyisobutylene Texas Petroleum Company 1350 (3500 Daltons), 20 grams
Aliphatic C-5 Hydrocarbon resin, Wingtack 95, 5 grams
d-limonene, 5 grams
t-butyl hydroquinone 0.5 gram
ascorbic palmitate 0.5 gram
vitamin A palmitate 0.2 gram
vitamin D2 0.1 gram
alpha-tocopherol 0.12 gram (500 IU/gram)
ferulic acid 0.6 gram
benzethonium chloride 0.5 gram This formula incorporated four vitamin antioxidants in lipophilic form, dissolved in the d-limonene which also functioned as a plasticizer for the adhesive mix. The elastomers were dissolved in the solvents, de-aerated, and the four vitamins were added and were spread onto a polyester/silicone release film using a 1.27 mm gap drawdown. The wet film was allowed to dry and was then covered with a backing fabric, 3M CoTran 9700 backing, a melt-blown polyurethane nonwoven material. The adhesive weight was about 33 mg/sq·cm and its thickness about 0.35 mm. Its bond to sheepskin was about 475 gm/cm width. It was found to remain in place on the cheek bone of the inventor for more than 48 hours.

In this formulation, the d-limonene serves multiple functions—a plasticizer for the polyisobutylenes, an oleophilic solvent for the anti-oxidant vitamins, and a permeant to penetrate into sebum follicles to help dissolve skin oils providing a lower viscosity and facilitating their removal by normal exudation and by ordinary soaps.

Example 10

A pressure-sensitive adhesive patch was prepared using the following formulation:

| | |
|---|---|
| BASF Oppanol 100 (polyisobutylene 1,100,000 Daltons) | 10 grams |
| Polyisobutylene Texas Petroleum Company 1350 (3500 Daltons) | 20 grams |
| Toluene | 70 grams |
| Wingtack 75 | 5 grams |
| d-Limonene | 5 grams |
| t-butyl hydroquinone | 0.5 gram |
| ascorbic palmitate | 0.5 gram |
| alfa tocopherol (500 IU/gram) | 0.5 gram |
| Vitamin A palmitate | 0.5 gram |
| Trisodium citrate | 0.5 gram |
| Mandelic acid | 0.25 gram (1%) |

This formulation used three vitamin anti-oxidants plus the hydroquinone antioxidant. Along with the multi-purpose d-limonene, the mandelic acid provides the dual function of oil-soluble anti-bacterial and exfoliant (combining the effects of benzoyl peroxide and salicylic acid) in a cosmetic formulation.

Example 11

A commercial silicone pressure-sensitive adhesive is thought to have a solubility parameter close to that of skin oils and thus may be a good "sponge" for excess skin oils. Dow Corning adhesive #282 was found to be about 58.8% solids with toluene and xylene listed as solvents. The following formula was prepared:

| | |
|---|---|
| Dow Corning 282 silicone adhesive | 34.6 grams (20 grams solids) |
| ascorbic palmitate | 0.44 gram |
| alpha tocopherol | 0.44 gram (500 IU/gram) |
| d-limonene | 0.6 gram |
| mandelic acid | 0.22 gram |
| methanol | 1.0 gram |
| dichloromethane | 5.09 gram |

This formulation was applied to a Teflon film with a drawdown blade having 1.27 mm gap, was allowed to blow-dry for about two hours and then 3M #3700 fabric was placed on the adhesive and was rolled in place, with further drying of the adhesive. The adhesive adhered strongly to the Teflon, thus it needs an alternative release surface such as a water-soluble film of polyvinyl alcohol which can then be washed off with water.

Benzoyl peroxide is not a preferred active ingredient in various embodiments. Benzoyl peroxide is reactive with the unsaturated oils of sebum and can polymerize them into waxes by reactions comparable to the vulcanization of synthetic elastomers such as done commercially with EPDM and dimethylsiloxane. Benzoyl peroxide is subject to slow decomposition at room temperature and at skin temperature, and any free radicals therefrom will likely react with unsaturated groups of the sebum oils causing polymerization into solids that will not exit the skin normally. This could exacerbate the acne problem. It may be suitable for use in an acne wash such as Example 2, as this treatment is intended to be wiped off soon after application to the skin. Addition of a small amount of oil-soluble anti-oxidant such as ascorbyl palmitate in Example 3 may be appropriate for minimizing pre-use decomposition of the benzoyl peroxide and for preventing cross-linking of the natural skin oils.

Although the above embodiments have been described in language that is specific to certain structures, elements, compositions, and methodological steps, it is to be understood that the technology defined in the appended claims is not necessarily limited to the specific structures, elements, compositions and/or steps described. Rather, the specific aspects and steps are described as forms of implementing the claimed technology. Since many embodiments of the technology can be practiced without departing from the spirit and scope of the invention, the invention resides in the claims hereinafter appended.

What is claimed is:

1. A formulation of a skin treatment effective in removal of sebum-formed oils from the skin of a human body, the formulation comprising:
glycerin, polyvinylpyrrolidone, salicylic acid, and two or more lipophilic vitamin anti-oxidants, and the polyvinylpyrrolidone in a crosslinked configuration by at least one of a chemical process or a radiation process, and the crosslinked configuration providing a complex of the salicycic acid with the polyvinylpyrrolidone so as to prevent the salicylic acid from permeation through the skin of the human body.

2. A pressure-sensitive adhesive patch configured for application over acne breakouts, the patch comprising:
a fabric material or flexible plastic backing material;
a formulation carried by the fabric material or the flexible plastic backing material, the formulation configured to provide a skin treatment effective in removal of sebum-formed oils from the skin of a human body, the formulation including glycerin, polyvinylpyrrolidone, salicylic acid, and two or more lipophilic vitamin anti-oxidants, and the polyvinylpyrrolidone in a crosslinked configuration by at least one of a chemical process or a radiation process after application of the formulation onto the fabric material or the flexible plastic backing material, and the crosslinked configuration providing a complex of the salicycic acid with the polyvinylpyrrolidone so as to prevent the salicylic acid from permeation through the skin of the human body.

3. The pressure-sensitive adhesive patch of claim 2, wherein the fabric material or the flexible plastic backing material includes an elastomeric adhesive having a solubility parameter between 13 and 20 $MPa^{0.5}$, and wherein the elastomeric adhesive contains a d-limonene plasticizer in a concentration between 0.5 and 10.0 weight percent.

4. The pressure-sensitive adhesive patch of claim 3, wherein the elastomeric adhesive is polybutene, polyisobutylene, or a mixture of polybutene and polyisobutylene.

5. The pressure-sensitive adhesive patch of claim 3, wherein the elastomeric adhesive has a silicone base.

6. The pressure-sensitive adhesive patch of claim 2, wherein the formulation contains mandelic acid in a concentration of between 0.5 and 5 weight percent.

7. The pressure-sensitive adhesive patch of claim 2, wherein the formulation contains two or more vitamin-based oleophilic anti-oxidants in a concentration exceeding 0.5 weight percent.

8. A method of treating skin blemishes including acne by placing an oil-absorbing patch over an incipient or mature pimple for at least 6 hours, the method comprising:
providing a pressure-sensitive adhesive patch configured for application over acne breakouts, the patch comprising:
a fabric material or flexible plastic backing material;
a formulation carried by the fabric material or the flexible plastic backing material, the formulation configured to provide a skin treatment effective in removal of sebum-formed oils from the skin of a human body, the formulation including glycerin, polyvinylpyrrolidone, salicylic acid, and two or more lipophilic vitamin anti-oxidants, and the polyvinylpyrrolidone in a crosslinked configuration by at least one of a chemical process or a radiation process after application of the formulation onto the fabric material or the flexible plastic backing material, and the crosslinked configuration providing a complex of the salicycic acid with the polyvinylpyrrolidone so as to prevent the salicylic acid from permeation through the skin of the human body;
placing the pressure-sensitive adhesive patch over an incipient or mature pimple for at least 6 hours; and
removing the pressure-sensitive adhesive patch from the incipient or mature pimple after placement thereon for at least 6 hours.

* * * * *